(12) United States Patent
Phillips

(10) Patent No.: US 7,544,693 B2
(45) Date of Patent: Jun. 9, 2009

(54) SPIROFUROPYRIDINE ARYL DERIVATIVES

(75) Inventor: Eifion Phillips, Boothwyn, PA (US)

(73) Assignee: AstraZeneca AB, Sodertalje (SE)

( * ) Notice: Subject to any disclaimer, the term of this patent is extended or adjusted under 35 U.S.C. 154(b) by 609 days.

(21) Appl. No.: 10/575,590

(22) PCT Filed: Oct. 21, 2004

(86) PCT No.: PCT/GB2004/004484

§ 371 (c)(1),
(2), (4) Date: Apr. 12, 2006

(87) PCT Pub. No.: WO2005/042538

PCT Pub. Date: May 12, 2005

(65) Prior Publication Data

US 2007/0072887 A1    Mar. 29, 2007

Related U.S. Application Data

(60) Provisional application No. 60/512,893, filed on Oct. 21, 2003.

(51) Int. Cl.
*A61K 31/438* (2006.01)
*C07D 491/22* (2006.01)
(52) U.S. Cl. .................................. 514/278; 546/18
(58) Field of Classification Search ............ 514/278; 546/18
See application file for complete search history.

(56) References Cited

FOREIGN PATENT DOCUMENTS

| WO | 00/42044 A | 7/2000 |
|---|---|---|
| WO | 02/096912 A | 12/2002 |
| WO | 03/087102 A | 10/2003 |
| WO | 03/087103 A | 10/2003 |

*Primary Examiner*—Charanjit S Aulakh
(74) *Attorney, Agent, or Firm*—Kenneth F. Mitchell

(57) ABSTRACT

Compounds of formula I:

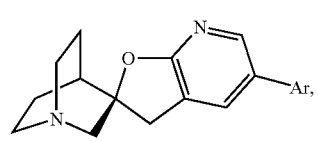

wherein Ar is a moiety of formula II or III:

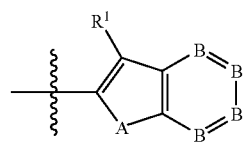

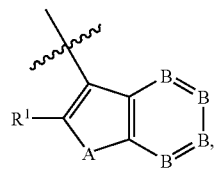

and pharmaceutically-acceptable salts thereof, wherein A, B, and $R^1$ are as defined in the specification, enantiomers, in vivo-hydrolysable precursors, pharmaceutical compositions and formulations containing them, methods of using them to treat diseases and conditions either alone or in combination with other therapeutically-active compounds or substances, processes and intermediates used to prepare them and uses of them for diagnostic and analytic purposes.

7 Claims, No Drawings

SPIROFUROPYRIDINE ARYL DERIVATIVES

RELATED APPLICATIONS

This is a National Phase Application of PCT/GB2004/004484, filed Oct. 21, 2004, which claims the priority of U.S. Provisional Application 60/512,893 filed Oct. 21, 2003.

TECHNICAL FIELD

This invention relates to novel spirofuropyridine aryl ligands for nicotinic acetylcholine receptors and their use in therapy.

BACKGROUND OF THE INVENTION

The use of compounds which bind to nicotinic acetylcholine receptors for the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease is discussed in: McDonald et al., (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; Williams et al., (1994) "Neuronal Nicotinic Acetylcholine Receptors," Drug News & Perspectives, vol. 7, pp. 205-223; Holladay et al. (1997) *J. Med. Chem.* 40(26), 4169-4194; Arneric and Brioni (Eds.) (1998) "Neuronal Nicotinic Receptors: Pharmacology and Therapeutic Opportunities", John Wiley & Sons, New York; Levin (Ed.) (2001) "Nicotinic Receptors in the Nervous System" CRC Press.

Compounds which bind to nicotinic acetylcholine receptors and particularly those that bind to alpha-7 nicotinic acetylcholine receptors are useful for the treatment of a range of disorders involving reduced cholinergic function such as Alzheimer's disease, cognitive or attention disorders, anxiety, depression, schizophrenia, analgesia, Tourette's syndrome, and Parkinson's disease. Such compounds are also useful for inducing smoking cessation and are neuroprotective.

SUMMARY OF THE INVENTION

The present invention encompasses spirofuropyridine aryl derivatives having activity at nicotinic acetylcholine receptors ("nAChRs"). Spirofuropyridine aryl derivatives of the invention are those in accord with formula I:

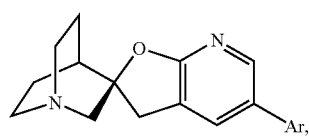

and pharmaceutically-acceptable salts thereof, wherein:

Ar is a moiety of formula II or III:

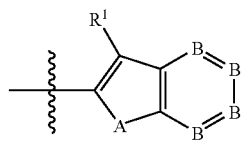

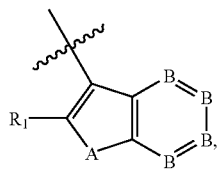

A is O or S;

B is N at one or two occurrences and $CR^1$ at all other occurrences;

$R^1$ is independently at each occurrence hydrogen, $-R^2$, $-C_2-C_6$alkenyl, $-C_2-C_6$alkynyl, halogen, $-CN$, $-NO_2$, $-NR^3R^4$ or $-OR^5$;

$R^2$ is an unsubstituted straight-chained, branched, or cyclic $C_1-C_6$alkyl group, or a straight-chained, branched, or cyclic $C_1-C_6$alkyl group substituted with 1, 2, 3, 4 or 5 halogen atoms, and 1 or 2 substituents selected from: $-C_2-C_6$alkenyl, $-C_2-C_6$alkynyl, $-CN$, $-NR^3R^4$, or $-OR^5$;

$R^3$ and $R^4$ are independently at each occurrence hydrogen, $R^5$, or in combination at any one occurrence of $-NR^3R^4$ are $-(CH_2)_pJ(CH_2)_q-$ wherein J is O, S, NH, $NR^5$ or a bond;

$R^5$ is an unsubstituted straight-chained, branched, or cyclic $C_1-C_6$alkyl group, or a straight-chained, branched, or cyclic $C_1-C_6$alkyl group substituted with 1, 2, 3, 4 or 5 halogen atoms;

p at each occurrence is 2, 3 or 4, and q at each occurrence is 0, 1 or 2.

The invention also encompasses enantiomers, in vivo-hydrolysable precursors and pharmaceutically-acceptable salts of the spirofuropyridine aryl derivatives, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

DETAILED DESCRIPTION OF THE INVENTION

In one aspect this invention comprises compounds that are potent ligands for nicotinic acetylcholine receptors (nAChRs).

Compounds of the invention are those in accord with formula I:

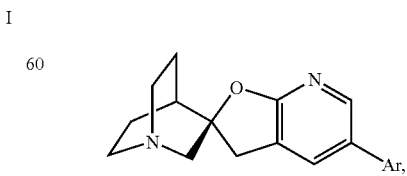

and pharmaceutically-acceptable salts thereof, wherein:

Ar is a moiety of formula II or III:

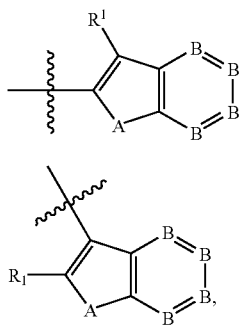

A is O or S;
B is N at one or two occurrences and CR¹ at all other occurrences;
R¹ is independently at each occurrence hydrogen, —R², —C₂-C₆alkenyl, —C₂-C₆alkynyl, halogen, —CN, —NO₂, —NR³R⁴ or —OR⁵;
R² is an unsubstituted straight-chained, branched, or cyclic C₁-C₆alkyl group, or a straight-chained, branched, or cyclic C₁-C₆alkyl group substituted with 1, 2, 3, 4 or 5 halogen atoms, and 1 or 2 substituents selected from: —C₂-C₆alkenyl, —C₂-C₆alkynyl, —CN, —NR³R⁴, or —OR⁵;
R³ and R⁴ are independently at each occurrence hydrogen, R⁵, or in combination at any one occurrence of —NR³R⁴ are —(CH₂)ₚJ(CH₂)ᵩ— wherein J is O, S, NH, NR⁵ or a bond;
R⁵ is an unsubstituted straight-chained, branched, or cyclic C₁-C₆alkyl group, or a straight-chained, branched, or cyclic C₁-C₆alkyl group substituted with 1, 2, 3, 4 or 5 halogen atoms;
  p at each occurrence is 2, 3 or 4, and
  q at each occurrence is 0, 1 or 2.
Particular compounds of the invention are those in which B is N at one occurrence and 3 or 4 occurrences of R¹ are hydrogen. Other particular compounds of the invention are those in which B is N at two occurrences and 2 or 3 occurrences of R¹ are hydrogen Other particular compounds of the invention are those in which B is N at one occurrence.

Other particular compounds of the invention are those in which Ar is formula IV:

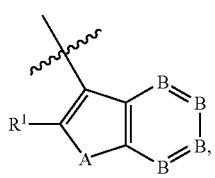

Further particular compounds of the invention are those in which A is O.

Compounds of the invention include:
(2'R)-5'-(furo[3,2-b]pyridine-3-yl)spiro{1-azabicyclo[2.2.2]octane-3,2'(3'H)-furo[2,3-b]pyridine};
(2'R)-5'-(furo[3,2-c]pyridine-3-yl)spiro{1-azabicyclo[2.2.2]octane-3,2'(3'H)-furo[2,3-b]pyridine};
(2'R)-5'-(furo[2,3-b]pyridine-3-yl)spiro{1-azabicyclo[2.2.2]octane-3,2'(3'H)-furo[2,3-b]pyridine}; and
(2'R)-5'-(furo[2,3-c]pyridine-3-yl)spiro{1-azabicyclo[2.2.2]octane-3,2'(3'H)-furo[2,3-b]pyridine}.

The invention also relates to compounds according to formula I, their use in therapy and compositions containing them.

Another aspect of the invention relates to compounds according to formula I wherein one or more of the atoms is labelled with a radioisotope of the same element. In one embodiment this aspect of the invention the compound of formula I is labelled with tritium.

Another aspect the invention relates to the use of compounds according to formula I for the therapy of diseases mediated through the action of nicotinic acetylcholine receptors. One embodiment of this aspect of the invention relates to the use of compounds of formula I for the therapy of diseases mediated through the action of α7 nicotinic acetylcholine receptors. Another embodiment of this aspect of the invention relates to the use for therapy, wherein the condition or disorder is Alzheimer's disease, learning deficit, cognition deficit, attention deficit, memory loss, Attention Deficit Hyperactivity Disorder. Another embodiment of this aspect of the invention relates to the use for therapy, wherein the disorder is anxiety, schizophrenia, or mania or manic depression. Another embodiment of this aspect of the invention relates to the use for therapy, wherein the disorder is Parkinson's disease, Huntington's disease, Tourette's syndrome, or neurodegenerative disorders in which there is loss of cholinergic synapses.

Another aspect of the invention relates to a use of a compound according to formula I in the manufacture of a medicament for the treatment or prophylaxis of human diseases or conditions in which activation of the α7 nicotinic receptor is beneficial. One embodiment of this aspect of the invention relates to a use of a compound according to formula I in the manufacture of a medicament for the treatment or prophylaxis of neurological or psychotic disorders or intellectual impairment disorders. Another embodiment of this aspect of the invention relates to the use of a compound according to formula I in the manufacture of a medicament for the treatment or prophylaxis of jetlag, for inducing the cessation of smoking, for treating nicotine addiction including that resulting from exposure to products containing nicotine, craving, pain, and for ulcerative colitis.

Another aspect of the invention relates to a method of treatment or prophylaxis of human diseases or conditions in which activation of the α7 nicotinic receptor is beneficial which comprises administering a therapeutically effective amount of a compound according to formula I. One embodiment of this aspect of the invention relates to a method of treatment or prophylaxis of neurological or psychotic disorders or intellectual impairment disorders, which comprises administering a therapeutically effective amount of a compound according to formula I. Another embodiment of this aspect of the invention relates to a method of treatment, wherein the disorder is Alzheimer's disease, learning deficit, cognition deficit, attention deficit, memory loss, or Attention Deficit Hyperactivity Disorder. Another embodiment of this aspect of the invention relates to a method of treatment, wherein the disorder is Parkinson's disease, Huntington's disease, Tourette's syndrome, or neurodegenerative disorders in which there is loss of cholinergic synapses. Another embodiment of this aspect of the invention relates to a method of treatment, wherein the disorder is anxiety, schizophrenia or mania or manic depression. Yet another embodiment of this aspect of the invention relates to a method of treatment or prophylaxis of jetlag, treatment for inducing cessation of smoking, treatment for nicotine addiction, craving, pain, and for ulcerative colitis, which comprises administering a therapeutically effective amount of a compound according to formula I.

Another aspect of the invention relates to a pharmaceutical composition comprising a compound according to formula I, and a pharmaceutically-acceptable diluent or carrier. Another embodiment of this aspect of the invention relates to a pharmaceutical composition for use in the treatment of prophylaxis of human diseases or conditions in which activation of the α7 nicotinic receptor is beneficial. Another embodiment of this aspect of the invention relates to a pharmaceutical composition for use in the treatment or prophylaxis of psychotic disorders or intellectual impairment disorders. Another embodiment of this aspect of the invention relates to a pharmaceutical composition for use in the treatment or prophylaxis of Alzheimer's disease, learning deficit, cognition deficit, attention deficit, memory loss, Attention Deficit Hyperactivity Disorder, anxiety, schizophrenia, or mania or manic depression Parkinson's disease, Huntington's disease, Tourette's syndrome, neurodegenerative disorders in which there is loss of cholinergic synapse, jetlag, for inducing the cessation of smoking, for treating nicotine addiction including that resulting from exposure to products containing nicotine, craving, and fro treating pain and ulcerative colitis. Yet another embodiment of this aspect of the invention relates to a pharmaceutical composition for treating or preventing a condition or disorder identified herein arising from dysfunction of nicotinic acetylcholine receptor neurotransmission in a mammal, preferably a human, comprising an amount of a compound of formula I, an enantiomer thereof or a pharmaceutically-acceptable salt thereof, effective in treating or preventing such disorder or condition and an inert pharmaceutically-acceptable carrier.

For the uses and methods of treatment described herein the dosage administered will, of course, vary with the compound employed, the mode of administration and the treatment desired. However, in general, satisfactory results will be obtained when the compounds of the invention are administered at a daily dosage of from about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The pharmaceutical compositions described herein will, of course, contain different quantities of compound depending on the compound employed. However, in general, compositions will provide from about 0.1 mg to about 20 mg per kg of animal body weight. Such doses may be given in divided doses 1 to 4 times a day or in sustained release form. For man, compositions will provide daily dose is in the range of from 5 mg to 1,400 mg, more preferably from 10 mg to 100 mg, and will provide unit dosage forms suitable for oral administration from 2 mg to 1,400 mg of the compound admixed with a solid or liquid pharmaceutical carriers, lubricants or diluents.

The compounds of formula I, or an enantiomer thereof, and pharmaceutically-acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically-acceptable diluent or carrier.

Examples of diluents and carriers are:
for tablets and dragees: lactose, starch, talc, stearic acid;
for capsules: tartaric acid or lactose;
for injectable solutions: water, alcohols, glycerine, vegetable oils;
for suppositories: natural or hardened oils or waxes.

There is also provided a process for the preparation of such a pharmaceutical composition that comprises mixing the ingredients.

A further aspect of the invention is the use of a compound according to the invention, an enantiomer thereof or a pharmaceutically-acceptable salt thereof, in the manufacture of a medicament for the treatment or prophylaxis of one of the below mentioned diseases or conditions; and a method of treatment or prophylaxis of one of the above mentioned diseases or conditions, which comprises administering a therapeutically effective amount of a compound according to the invention, or an enantiomer thereof or a pharmaceutically-acceptable salt thereof, to a patient.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds that are or are also agonists of the α4 nAChR subtype. Therefore, compounds that are selective for the α7 nAChR subtype are preferred. The compounds of the invention are indicated as pharmaceuticals, in particular in the treatment or prophylaxis of psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, craving, and for the treatment or prophylaxis of nicotine addiction (including that resulting from exposure to products containing nicotine).

It is also believed that compounds according to the invention are useful in the treatment and prophylaxis of ulcerative colitis.

As used herein, the term "$C_{1-6}$ alkyl" refers to a straight-chained, branched, or cyclic $C_{1-6}$ alkyl group.

Radio-Labelled Forms

Another aspect of the invention relates to radio-labelled forms of the compounds of the invention. Such compounds that bind potently and selectively to a receptor are useful because sensitive and quantitative techniques are available for the detection of the radioactivity, which allow the interaction of a compound with its receptor to be detected and measured.

One method of discovering compounds that bind to a receptor is to perform a binding assay where the degree of displacement of a radio-labelled compound by another compound is measured. Thus, radio-labelled forms of compounds that potently bind receptors are useful to screen for novel medicinal compounds that bind to receptors. Such novel medicinal compounds may modulate the activity of those receptors by agonism, partial-agonism, or antagonism. Radio-labelled forms of compounds of the invention are therefore useful in a screen for the discovery of other compounds that bind to nicotinic receptors.

The ability of analogue compounds to bind to localized receptors within the body makes it possible to utilize such compounds for in situ imaging by PET, SPECT and similar imaging methods. PET imaging is accomplished with the aid of tracer compounds labelled with a positron-emitting isotope: Goodman, M. M. Clinical Positron Emission Tomography, Mosby Yearbook, 1992, K. F. Hubner et al., Chapter 14.

For most biological targets, few isotopes are suitable. The carbon isotope, $^{11}C$, has been used for PET, but its short half-life of 20.5 minutes limits its usefulness to compounds that can be synthesized and purified quickly, and to facilities that are proximate to a cyclotron where the precursor $^{11}C$ starting material is generated. Other more energetic isotopes have even shorter half-lives, $^{13}N$ has a half-life of 10 minutes and $^{15}O$ has a half-life of two minutes. Nevertheless, PET studies have been carried out with these isotopes as described by Hubner, K. F., in Clinical Positron Emission Tomography, Mosby Year Book, 1992, K. F. Hubner, et al., Chapter 2. [$^{18}F$]-labelled compounds have been used in PET studies, but their use is limited by the 110-minute half-life of the isotope. Most notably, [$^{18}F$]-fluorodeoxyglucose has been widely used in studies of glucose metabolism and localization of glucose uptake associated with brain activity. [$^{18}F$]-L-fluorodopa and other dopamine receptor analogues have also been used in mapping dopamine receptor distribution.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analogue binding, localization and clearance rates. A isotope used for SPECT imaging is $^{123}I$, a γ-emitter with a 13.3 hour half life. Compounds labelled with $^{123}I$ can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Increasingly, the precise location and distribution of receptors in the brain and other tissues is of interest to clinical researchers, clinicians and diagnosticians. The distribution of nAChR's in the brains of individuals having disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease is of growing interest as the molecular bases of these conditions is being discovered. The precise location and distribution of nAChRs in the brain and other tissues is also of importance in assessing the relevance of animal models of these conditions.

Methods of Preparation

Methods that may be used for the synthesis of compounds of formula I include the method outlined in Scheme 1. Unless otherwise noted Ar in Scheme 1 is as defined above for Formula 1.

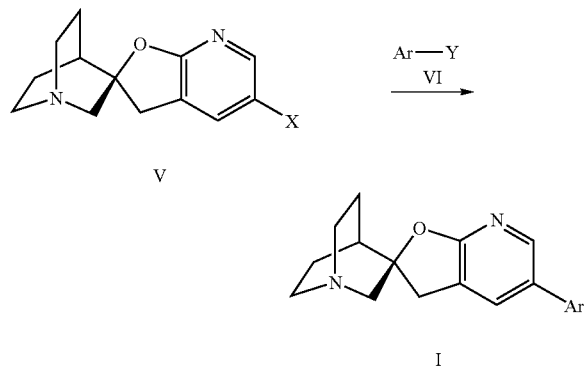

Scheme 1

The compounds of formula I cross-coupling reaction of compounds of formula V and VI, wherein either X or Y is halogen or $OSO_2CF_3$ when, respectively, Y or X is an organometallic group. Suitable organometallic groups include boronic acid or boronic ester groups, $B(OH)_2$, $B(OAlk)_2$ or a trialkylstannyl group $SnAlk_3$, wherein Alk is an alkyl group. The reaction is performed in the presence of a suitable organometallic catalyst and solvent. Suitable organometallic catalysts include palladium (0) complexes, for example tetrakis (triphenylphosphine)palladium(0) or a combination of tris (dibenzylideneacetone)dipalladium(0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula V or VI is a boronic acid, the presence of a suitable base in addition to the other reagents is preferred. Suitable bases include sodium carbonate, cesium carbonate, and barium hydroxide. The reaction is carried out at a temperature of 0-120° C., and preferably at a temperature of 60-120° C.

Compounds of formula V wherein X is an organometallic group or compounds of formula VI, wherein Y is an organometallic group may be prepared from compounds of the corresponding formula wherein X or Y as appropriate is hydrogen, halogen, or $OSO_2CF_3$ by a suitable metallation or exchange procedure. The compounds wherein the organometallic group is $B(OH)_2$ may be prepared from suitable aromatic compounds having hydrogen or halogen groups, by conversion to the corresponding aryllithium or arylmagnesium compounds followed by reaction with trialkylborate and subsequent hydrolysis of the resulting borate ester. Similarly, compounds wherein the organometallic group is a trialkylstannyl group may be prepared from suitable aromatic compounds having hydrogen or halogen groups, by conversion to the corresponding aryllithium or arylmagnesium compounds followed by reaction with an appropriate trialkylstannyl halide. The formation of the aryllithium or arylmagnesium compound is performed in a suitable inert solvent, for example, tetrahydrofuran. Alternatively, the compounds wherein the organometallic group is $B(OH)_2$ may be prepared from suitable aromatic compounds having halogen or $OSO_2CF_3$ groups by reaction with bis(pinacolato)diboron and an organometallic catalyst, followed by hydrolysis of the resulting borate ester. Compounds wherein the said organometallic group is a trialkylstannyl group may be prepared from suitable aromatic compounds having halogen or $OSO_2CF_3$ groups by reaction with the appropriate bis(trialkyltin) in the presence of a suitable organometallic catalyst. The reaction is performed in a suitable inert solvent, for example tetrahydrofuran, and suitable organometallic catalyst include, for example tetrakis(triphenylphosphine). The reaction is performed at a temperature of about 0° C. to about 150° C., preferably about 20° C. to about 100° C. Typical procedures for effecting such conversions will be known to those of skill in the art.

Compounds of formula V or VI wherein X or Y as appropriate represents $OSO_2CF_3$ may be prepared from compounds of formula V or VI wherein X or Y represents OH by reaction with trifluoromethanesulfonic anhydride or other trifluoromethanesulfonylating agent in the presence of a base and a suitable solvent. Suitable bases include pyridine, and 2,6-di-t-butylpyridine. The reaction is preferably performed at a temperature of −78 to 120° C., and most preferably at a temperature of −78 to 0° C.

Compounds of formula V may be prepared by the methods described in international patent application publication number WO99/03859.

Compounds of formula VI may be prepared by methods described herein, are known in the literature, may be prepared by methods adapted from methods described herein or in the literature by a person skilled in the art of synthetic organic chemistry, or may be prepared by methods known or which will be apparent to a person skilled in the art of synthetic organic chemistry.

Radio-labelled forms of compounds of the invention are synthesized either by incorporating radio-labelled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Where necessary, hydroxy, amino, or other reactive groups may be protected using a protecting group as described in the standard text "Protecting groups in Organic Synthesis", $3^{rd}$ Edition (1999) by Greene and Wuts.

The above-described reactions, unless otherwise noted, are usually conducted at a pressure of about one to about three atmospheres, preferably at ambient pressure (about one atmosphere).

Unless otherwise stated, the above-described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts. Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallisation, or chiral HPLC. Alternatively the individual enantiomers may be made by reaction of the appropriate optically active starting materials under reaction conditions that will not cause racemisation.

Pharmacology

The pharmacological activity of compounds of the invention may be measured using the tests set out below:

Test A—Assay for Affinity at α7 nAChR Subtype

[$^{125}$I]-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30-80 μg) were incubated with 5 nM [$^{125}$I]α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 μM (−)-nicotine, and specific binding was typically 75%.

Test B—Assay for Affinity to the α4 nAChR Subtype

[$^3$H]-(−)-nicotine binding. Using a procedure modified from Martino-Barrows and Kellar (Mol Pharm (1987) 31:169-174), rat brain (cortex and hippocampus) was homogenized as in the [$^{125}$I]α-BTX binding assay, centrifuged for 20 minutes at 12,000×g, washed twice, and then resuspended in HB containing 100 μM diisopropyl fluorophosphate. After 20 minutes at 4° C., membranes (approximately 0.5 mg) were incubated with 3 nM [$^3$H]-(−)-nicotine, test drug, 1 μM atropine, and either 2 mM $CaCl_2$ or 0.5 mM EGTA for 1 h at 4° C., and then filtered over Whatman glass fiber filters (thickness C) (pretreated for 1 h with 0.5% PEI) using a Brandel cell harvester. Nonspecific binding was described by 100 μM carbachol, and specific binding was typically 84%.

Binding Data Analysis for Tests A and B $IC_{50}$ values and pseudo Hill coefficients (nH) were calculated using the non-linear curve-fitting program ALLFIT (DeLean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding KD values of 1.67 and 1.70 nM for the [$^{125}$I]-α-BTX and [3H]-(−)-nicotine ligands respectively. Ki values were estimated using the general Cheng-Prusoff equation:

$$Ki = [IC_{50}]/((2+([ligand]/[KD])n)1/n - 1)$$

where a value of n=1 was used whenever nH<1.5 and a value of n=2 was used when nH≧1.5. Samples were assayed in triplicate and were typically ±5%. Ki values were determined using 6 or more drug concentrations. The compounds of the invention are compounds with binding affinities (Ki) of less than 1000 nM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

EXAMPLES

Commercial reagents were used without further purification. n-Butyllithium was used as a solution in hexane. Mass spectra were recorded using an HPLC-MS system employing an HP-1100 HPLC and a Micromass LCZ Mass Spectrometer using APCI as the ionisation technique, an HPLC-MS system employing an HP-1100 HPLC and an HP-1100-series mass selective detector using APCI as the ionisation technique, or a GC-MS system employing an HP-6890 gas chromatograph and an HP-5973 mass selective detector employing electron impact ionisation, and are reported as m/z for the parent molecular ion. Room temperature refers to 20-25° C. 5'-Bromospiro[1-azabicyclo[2.2.2]octane-3,2'(3'H)-furo[2,3-b]pyridine] and other precursors were prepared as described in international patent application publication number WO 99/03859.

Preparation 1

(2'R)-5'-Trimethylstannyl-spiro[1-azabicyclo[2.2.2]
octane-3.2'(3'H)-furo[2,3-b]pyridine]

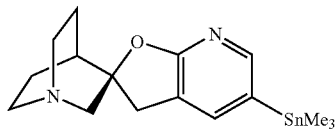

(2'R)-5'-Bromospiro[1-azabicyclo[2.2.2]octane-3,2'(3'H)-furo[2,3-b]pyridine] (690 mg, 2.34 mmol), hexamethylditin (1.225 g, 0.27 mmol) and tetrakis(triphenylphosphine)palladium (0) (266 mg, 0.027 mmol) were mixed with 10 mL of toluene and sealed under nitrogen. The mixture was stirred and heated at 120° C. under nitrogen for 4 h. The mixture was then allowed to cool and filtered through diatomaceous earth. The filtrate was diluted with chloroform, washed with saturated sodium bicarbonate, dried through MgSO$_4$, filtered, and the solvent was evaporated. Purification by flash chromatography using a gradient of ammoniated methanol in chloroform gave the title compound as a solid (780 mg); m/e 377 379 381 (MH$^+$).

Example 1

(2'R)-5'-(Furo[3,2-b]pyridine-3-yl)spiro{1-azabicyclo[2.2.2]octane-3,2'(3'H)-furo[2,3-b]pyridine}

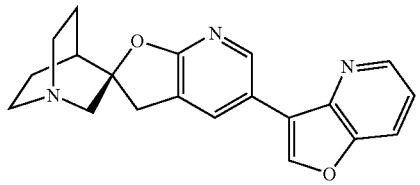

(a) Furo[3,2-b]pyridin-3-yl
trifluoromethanesulfonate

3-Hydroxy-picolinic acid (15.6 g, 42.1 mmol), ethanol (360 mL), benzene (100 mL) and 98% sulfuric acid (6 mL) were heated under reflux for 40 h. After evaporation of the ethanol and benzene, the residue was dissolved in water, neutralized with sodium bicarbonate, and extracted with chloroform. The organic layer was dried (MgSO$_4$), filtered, and then the solvent was evaporated to give ethyl 3-hydroxy-picolinate as a brown oily residue (11.0 g).

A mixture of ethyl 3-hydroxy-picolinate (11.0 g, 65.8 mmol), ethyl bromoacetate (12.1 g, 72.4 mmol) and anhydrous potassium carbonate (11.8 g, 85.5 mmol) in acetone (120 mL) was heated under reflux for 15 h. After cooling, the inorganic material separated by filtration. The filtrate was dissolved in chloroform, washed with water, then brine and dried (MgSO$_4$), filtered, and the solvent was evaporated to give a brown oily residue. The residue was purified by flash chromatography using a gradient of ammoniated methanol in chloroform to give ethyl 2-(2-ethoxycarbonyl-3-pyridyloxy)acetate (13.7 g) as a yellow oil (13.7 g).

Ethyl 2-(2-ethoxycarbonyl-3-pyridyloxy)acetate (13.6 g, 54.0 mmol) and sodium ethoxide (8.08 g, 118.8 mmol) in toluene (200 mL) were heated under reflux for 18 h. After cooling, a precipitate was collected by filtration, dissolved in the minimum amount of hot water (about 300 mL), and acidified with acetic acid (6 mL). The resulting precipitate was filtered, and dried in vacuo to give ethyl 3-hydroxyfuro[3,2-b]pyridine-2-carboxylate as a solid (7.0 g).

Ethyl 3-hydroxyfuro[3,2-b]pyridine-2-carboxylate (6.90 g, 25.8 mmol) was dissolved in 10% hydrochloric acid (50 mL), and heated under reflux for 3 h. Evaporation of the hydrochloric acid solution gave furo[3,2-b]pyridin-3(2H)-one hydrochloride (9.0 g). A portion of the furo[3,2-b]pyridin-3(2H)-one hydrochloride was converted to its free base by treatment with saturated sodium bicarbonate and extraction with chloroform in preparation for the following step.

N,N-Diisopropylethylamine (1.08 g, 8.34 mmol) was added slowly to a solution of furo[3,2-b]pyridin-3(2H)-one (1.40 g, 7.25 mmol) in dry dichloromethane (60 mL) under nitrogen at −10° C. Then trifuromethanesulfonic anhydride (2.45 g, 8.70 mmol) was added slowly. The mixture was warmed to RT, and stirred overnight. The reaction was quenched with water. The organic layer was washed with water and brine, dried (MgSO$_4$), and then the solvent was evaporated to give a brown oily residue, which was purified by flash chromatography using chloroform to give the subtitle compound (980 mg) as a light-brown oil.

(b) (2'R)-5'-(Furo[3,2-b]pyridine-3-yl)spiro[1-azabicyclo[2.2.2]octane-3.2'(3'H)-furo[2,3-b]pyridine]

(2'R)-5'-Trimethylstannyl-spiro[1-azabicyclo[2.2.2]octane-3,2'(3'H)-furo[2,3-b]pyridine] (200 mg, 0.53 mmol), furo[3,2-b]pyridine-3-triflate (184 mg, 0.69 mmol), Pd$_2$dba$_3$ (25 mg, 0.027 mmol) and triphenylphosphine (14 mg, 0.053 mmol) were mixed in 2 mL of DMF. The reaction was heated to 100° C. for six hours. After cooling, the mixture was poured into a solution of brine, and extracted with chloroform. The organic layer was dried through MgSO$_4$, and the solvent was evaporated. The residue was purified by flash chromatography using a gradient of ammoniated methanol in chloroform to give a solid. The solid was further purified by reverse phase HPLC on a Waters Novapak-HR C$_{18}$ Column using a gradient of 5-45% acetonitrile/water as the eluant (each solvent containing 0.1% trifluoroacetic acid as a buffer). The product-containing fractions were evaporated. The residue was neutralized with NaHCO3, extracted with chloroform, and the solvent was evaporated to give the title compound (33 mg) as a white solid; m/e 334.3 (MH$^+$).

Example 2

(2'R)-5'-(Furo[3,2-c]pyridine-3-yl)spiro[1-azabicyclo[2.2.2]octane-3.2'(3'H)-furo[2,3-b]pyridine]

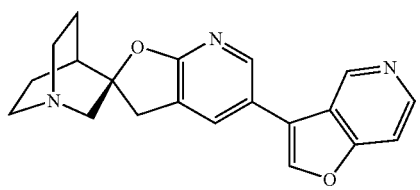

(a) Furo[3,2-c]pyridin-3-yl
trifluoromethanesulfonate

To a solution of 4-chloronicotinic acid (7.03 g, 44.6 mmol) in 100 mL of hexamethylphosphoric triamide (HMPA) was added a solution of 5.5 N sodium hydroxide (13 mL) at 0° C.

Then iodoethane (27.8 g, 179 mmol) was added into the reaction mixture at 0° C. over 1 h, and stirring was continued for a further 1 h at room temperature. The mixture was diluted with 250 mL of water, and then extracted three times with ether. The ethereal extracts were combined, washed three times with water, then dried (MgSO$_4$), filtered, and the solvent was evaporated to give ethyl 4-chloronicotinate (6.21 g) as a brown oily residue, which was used for the next step without further purification.

Ethyl glycolate (7.26 g, 59.7 mmol) was added slowly into a suspension of sodium hydride (2.95 g of 60% dispersion in mineral oil, 73.8 mmol) in 85 mL of 1,2-dimethoxyethane (DME) at 0° C., and the mixture was stirred for another 30 min. A solution of ethyl 4-chloronicotinate (6.20 g, 33.4 mmol) in 20 mL of DME was added slowly into the reaction mixture at room temperature. The mixture was heated to 70° C. and maintained at that temperature overnight. The solvent was evaporated and the residue was dissolved in 100 mL of water, and washed with hexane 3 times. The pH of the water solution was adjusted to about 5 using acetic acid to pH 5, and a yellow precipitate was formed. The yellow precipitate was filtered, washed with a small amount of water (20 mL×3), and dried overnight in vacuo to give ethyl 3-hydroxyfuro[3,2-c]pyridine-2-carboxylate free base as a yellow solid (5.79 g) which was used for the next step without further purification.

Ethyl 3-hydroxyfuro[3,2-c]pyridine-2-carboxylate (5.79 g, 27.9 mmol) was dissolved in 10% hydrochloric acid (50 mL), and heated under reflux for 40 h. The reaction mixture was evaporated to dryness. The residue was suspended in saturated sodium bicarbonate solution and extracted with chloroform 3 times. The chloroform extracts were combined, dried (MgSO$_4$), filtered, and evaporated to give furo[3,2-c]pyridin-3(2H)-one (570 mg) as a light-brown oil. N,N-Diisopropylethylamine (616 mg, 4.77 mmol) was added slowly to a solution of furo[3,2-c]pyridin-3(2H)-one (560 mg, 4.14 mmol) in dry methylene chloride (25 mL) under nitrogen at −10° C. Then trifluoromethanesulfonic anhydride (1.40 g, 4.97 mmol) was added slowly. The mixture was allowed to warm to RT, and stirred for another 1 g. The reaction was quenched with water. The organic layer was washed with water, dried (MgSO$_4$), filtered, and then the solvent was evaporated to give the sub-title compound as a brown oily residue (1.10 g), which was used without further purification for the next step.

(b) (2'R)-5'-(Furo[3,2-c]pyridine-3-yl)spiro[1-azabicyclo[2.2.2]octane-3,2'(3'H)-furo[2,3-b]pyridine]

Prepared by a method analogous to that described for the preparation of Example 1 from (2'R)-5'-trimethylstannylspiro[1-azabicyclo[2.2.2]octane-3,2'(3'H)-furo[2,3-b]pyridine] and furo[3,2-c]pyridin-3-yl trifluoromethanesulfonate. After reverse phase chromatography, the title compound was obtained as the trifluoroacetate salt which was a colourless solid; m/e 334 (MH$^+$).

Example 3

(2'R)-5'-Furo[2,3-b]pyridine-3-yl spiro{-azabicyclo[2.2.2]octane-3,2'(3'H)-furo[2,3-b]pyridine}

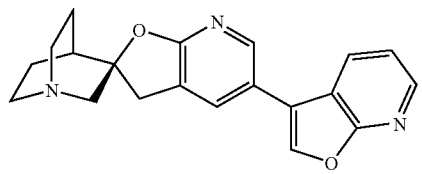

(a) Furo[2,3-b]pyridin-3-yl trifluoromethanesulfonate

2-Chloronicotinic acid (5.90 g, 37.5 mmol), ethanol (120 mL), toluene (35 mL) and 98% sulfuric acid (2 mL) were heated together under reflux for 48 hours. After evaporation of the ethanol and toluene, the residue was dissolved in water, neutralized with sodium bicarbonate, and extracted with chloroform. The organic layer was dried through MgSO$_4$, and then the solvent was evaporated to give a dark-brown oil-like residue, which was purified by flash chromatography using a gradient of 10-20% hexane/ethyl acetate as the eluant to give ethyl 2-chloronicotinate (4.60 g) as a light-brown oil.

Ethyl glycolate (7.00 g, 67.3 mmol) was added slowly into a suspension of sodium hydride (2.80 g of 60% dispersion in mineral oil, 70.0 mmol) in 60 mL of 1,2-dimethoxyethane (DME) at 0° C., and the mixture was then stirred for another 30 min. A solution of ethyl 2-chloronicotinate (4.60 g, 24.8 mmol) in 14 mL of DME was added into the reaction mixture slowly at room temperature. Then the mixture was heated at 70° C. overnight. After evaporation of the solvent, the residue was dissolved in 90 mL of water, washed three times with hexane, acidified with acetic acid, and extracted three times with chloroform. The combined chloroform layers were dried (MgSO$_4$), and evaporated to give a yellow residue. The residue was crystallized from 20 mL of ether to give ethyl 3-hydroxyfuro[2,3-b]pyridine-2-carboxylate as a pale-yellow solid (4.30 g).

Ethyl 3-hydroxyfuro[2,3-b]pyridine-2-carboxylate (3.0 g, 11.23 mmol) was heated under reflux in 10% hydrochloric acid (50 mL) for 3 h. Evaporation of the hydrochloric acid solution gave furo[2,3-b]pyridin-3(2H)-one as the hydrochloride salt (1.73 g). A portion of the furo[2,3-b]pyridin-3(2H)-one hydrochloride was converted to its free base by treated with saturated sodium bicarbonate and extracted with chloroform in preparation for the following step.

N,N-Diisopropylethylamine (429 mg, 3.32 mmol) was added slowly to a solution of furo[2,3-b]pyridin-3(2H)-one (390 mg, 3.89 mmol) in dry dichloromethane under nitrogen at −10° C. Then, trifluromethanesulfonic anhydride (978 mg, 3.47 mmol) was added slowly. The mixture was allowed to warm to RT, and stirred for another 2 h. The reaction was quenched with water. The organic layer was washed with water, and then dried (MgSO$_4$), filtered, and then the solvent was evaporated to give a brown oily residue. Purification by flash chromatography using chloroform to give the sub-title compound as a light-brown oil (576 mg).

(b) (2'R)-5'-(Furo[2,3-b]pyridine-3-yl)spiro[1-azabicyclo[2.2.2]octane-3,2'(3'H)-furo[2,3-b]pyridine]

Prepared by a method analogous to that described for the preparation of Example 1 from (2'R)-5'-trimethylstannylspiro[1-azabicyclo[2.2.2]octane-3,2'(3'H)-furo[2,3-b]pyridine] and furo[2,3-b]pyridin-3-yl trifluoromethanesulfonate. The title compound was obtained as a colourless solid; m/e 334 (MH$^+$).

Example 4

(2'R)-5'-(Furo[2,3-c]pyridine-3-yl)spiro{1-azabicyclo[2.2.2]octane-3.2'(3'H)-furo[2,3-b]pyridine}

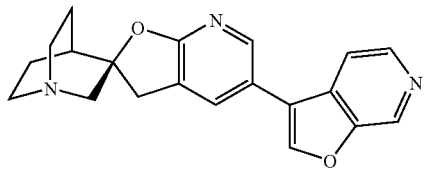

The title compound is prepared by a synthesis analogous to that described in the synthesis of Example 1 starting from 3-hydroxypyridine-4-carboxylic acid [Di Marco et al., *Eur. J. Inorg. Chem.*, 2002, (10), 2648-2655].

The invention claimed is:
1. A compound of formula I:

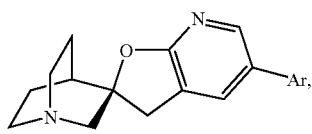

I or a pharmaceutically-acceptable salt thereof, wherein:
Ar is a moiety of formula II or III:

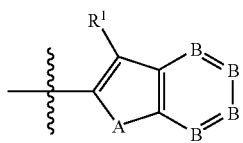

II

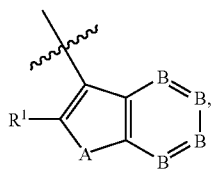

III wherein,
A is O or S;
B is N at one or two occurrences and CR$^1$ at all other occurrences;

R$^1$ is independently at each occurrence hydrogen, —R$^2$, —C$_2$-C$_6$alkenyl, —C$_2$-C$_6$alkynyl, halogen, —CN, —NO$_2$, —NR$^3$R$^4$ or —OR$^5$;

R$^2$ is an unsubstituted straight-chained, branched, or cyclic C$_1$-C$_6$alkyl group, or a straight-chained, branched, or cyclic C$_1$-C$_6$alkyl group substituted with 1, 2, 3, 4 or 5 halogen atoms, and 1 or 2 substituents selected from: C$_2$-C$_6$alkenyl, C$_2$-C$_6$alkynyl, —CN, —NR$^3$R$^4$, or —OR$^5$;

R$^3$ and R$^4$ are independently at each occurrence hydrogen, R$^5$, or in combination at any one occurrence of —NR$^3$R$^4$ are —(CH$_2$)$_p$J(CH$_2$)$_q$— wherein J is O, S, NH, NR$^5$ or a bond;

R$^5$ is an unsubstituted straight-chained, branched, or cyclic C$_1$-C$_6$alkyl group, or a straight-chained, branched, or cyclic C$_1$-C$_6$alkyl group substituted with 1, 2, 3, 4 or 5 halogen atoms;

p at each occurrence is 2, 3, or 4;
q at each occurrence is 0, 1, or 2.

2. A compound according to claim 1 or a pharmaceutically-acceptable salt thereof, selected from compounds wherein B is N at one occurrence and 2 or 3 occurrences of R$^1$ are hydrogen, or compounds wherein B is N at two occurrences and 1 or 2 occurrences of R$^1$ are hydrogen.

3. A compound according to claim 1 wherein B is N at one occurrence.

4. A compound according to claim 1 or a pharmaceutically-acceptable salt thereof, wherein Ar is formula III:

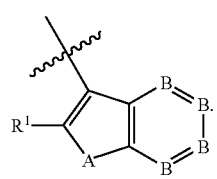

III

5. A compound according to claim 1 or a pharmaceutically-acceptable salt thereof, wherein A is O.

6. A compound according to claim 1, selected from the group consisting of:
(2'R)-5'-(furo[3,2-b]pyridine-3-yl)spiro{1-azabicyclo[2.2.2]octane-3,2'(3'H)-furo[2,3-b]pyridine};
(2'R)-5'-(furo[3,2-c]pyridine-3-yl)spiro{1-azabicyclo[2.2.2]octane-3,2'(3'H)-furo[2,3-b]pyridine};
(2'R)-5'-(furo[2,3-b]pyridine-3-yl)spiro{1-azabicyclo[2.2.2]octane-3,2'(3'H)-furo[2,3-b]pyridine}; and
(2'R)-5'-(furo[2,3-c]pyridine-3-yl)spiro{1-azabicyclo[2.2.2]octane-3,2'(3'H)-furo[2,3-b]pyridine}.

7. A pharmaceutical composition comprising a compound according to claim 1, and a pharmaceutically-acceptable diluent or carrier.

* * * * *